US010966618B2

(12) United States Patent
Natsui et al.

(10) Patent No.: US 10,966,618 B2
(45) Date of Patent: Apr. 6, 2021

(54) LIFESAVING ASSISTING APPARATUS (71) Applicants: NIHON KOHDEN CORPORATION, Tokyo (JP); KYOTO UNIVERSITY, Kyoto (JP)

(72) Inventors: Tomoyoshi Natsui, Tokyo (JP); Satoshi Hayashi, Tokyo (JP); Tsutomu Wakabayashi, Tokyo (JP); Taku Iwami, Kyoto (JP); Toshihiro Hatakeyama, Kyoto (JP); Tetsuro Nishimura, Osaka (JP); Takayuki Otani, Suita (JP)

(73) Assignees: NIHON KOHDEN CORPORATION, Tokyo (JP); KYOTO UNIVERSITY, Kyotos (JP)

( * ) Notice: Subject to any disclaimer, the term of this patent is extended or adjusted under 35 U.S.C. 154(b) by 609 days.

(21) Appl. No.: 15/745,342

(22) PCT Filed: Jul. 13, 2016

(86) PCT No.: PCT/JP2016/003318
§ 371 (c)(1),
(2) Date: Jan. 16, 2018

(87) PCT Pub. No.: WO2017/013856
PCT Pub. Date: Jan. 26, 2017

(65) Prior Publication Data
US 2018/0206748 A1    Jul. 26, 2018

(30) Foreign Application Priority Data

Jul. 17, 2015  (JP) .............................. JP2015-143008
May 12, 2016  (JP) .............................. JP2016-096356

(51) Int. Cl.
*A61B 5/024*    (2006.01)
*A61B 5/1455*   (2006.01)
(Continued)

(52) U.S. Cl.
CPC ...... *A61B 5/02433* (2013.01); *A61B 5/14552* (2013.01); *A61B 5/7405* (2013.01); *A61N 1/39* (2013.01); *A61B 5/026* (2013.01)

(58) Field of Classification Search
CPC .............. A61B 5/1455; A61B 5/14551; A61B 5/14552; A61B 5/7405; A61B 5/024;
(Continued)

(56) References Cited

U.S. PATENT DOCUMENTS

2001/0047140 A1   11/2001  Freeman
2002/0002339 A1   1/2002   Sugo et al.
(Continued)

FOREIGN PATENT DOCUMENTS

CN   101031242 A   9/2007
JP   2001-321347 A  11/2001
(Continued)

OTHER PUBLICATIONS

Communication dated May 7, 2020 issued by the Japanese Intellectual Property Office in counterpart Japanese Application No. 2016-096356.
(Continued)

*Primary Examiner* — Eric F Winakur
*Assistant Examiner* — Chu Chuan Liu
(74) *Attorney, Agent, or Firm* — Sughrue Mion, PLLC (57) ABSTRACT A light-emitting section (21) emits light to be irradiated on a body of a patient (100). A light-receiving section (22) outputs a signal corresponding to an intensity of light which has been transmitted through or reflected from the body of the patient (100). A pulse-amplitude Index acquiring section (32) analyzes amplitude of the signal to acquire a pulse-amplitude Index of the patient (100). A pulse determining section (33) determines presence or absence of a pulse of the patient (100) in accordance with the pulse-amplitude Index.

(Continued)

A notifying section (34) notifies a result of determination made by the pulse determining section (33).

10 Claims, 6 Drawing Sheets

(51) Int. Cl.
*A61B 5/00* (2006.01)
*A61N 1/39* (2006.01)
*A61B 5/026* (2006.01)

(58) Field of Classification Search
CPC . A61B 5/02416; A61B 5/026; A61B 5/02443; A61B 5/0205; A61B 5/68; A61B 5/6801; A61B 5/6802; A61B 5/6813; A61B 5/6814
See application file for complete search history.

(56) References Cited

U.S. PATENT DOCUMENTS

| | | | |
|---|---|---|---|
| 2003/0055458 A1 | 3/2003 | Hamilton et al. | |
| 2003/0083699 A1 | 5/2003 | Hamilton et al. | |
| 2003/0236647 A1* | 12/2003 | Yoon | A61B 5/14551 702/183 |
| 2004/0116969 A1 | 6/2004 | Owen et al. | |
| 2004/0176807 A1 | 9/2004 | Freeman | |
| 2004/0267324 A1* | 12/2004 | Geheb | A61B 5/6833 607/5 |
| 2005/0131465 A1 | 6/2005 | Freeman et al. | |
| 2005/0197672 A1 | 9/2005 | Freeman | |
| 2005/0250997 A1 | 11/2005 | Takeda et al. | |
| 2006/0064131 A1 | 3/2006 | Freeman et al. | |
| 2006/0200203 A1 | 9/2006 | Hamilton et al. | |
| 2008/0015439 A1 | 1/2008 | Raju et al. | |
| 2008/0046015 A1 | 2/2008 | Freeman et al. | |
| 2008/0071316 A1 | 3/2008 | Freeman | |
| 2008/0077010 A1 | 3/2008 | Cohen-Solal et al. | |
| 2011/0015688 A1 | 1/2011 | Hamilton et al. | |
| 2011/0112593 A1 | 5/2011 | Freeman et al. | |
| 2012/0150244 A1 | 6/2012 | Freeman et al. | |
| 2012/0191149 A1 | 7/2012 | Freeman | |
| 2012/0220573 A1 | 8/2012 | Gosmini et al. | |
| 2012/0252781 A1 | 10/2012 | Bailey et al. | |
| 2013/0324855 A1 | 12/2013 | Lisogurski et al. | |
| 2014/0155787 A1 | 6/2014 | Freeman et al. | |
| 2014/0247274 A1 | 9/2014 | Nagata | |
| 2015/0210706 A1 | 7/2015 | Gosmini et al. | |
| 2015/0299210 A1 | 10/2015 | Bailey et al. | |
| 2015/0352000 A1 | 12/2015 | Freeman | |
| 2016/0287860 A1 | 10/2016 | Freeman | |
| 2017/0049385 A1 | 2/2017 | Freeman et al. | |
| 2017/0145021 A1 | 5/2017 | Bailey et al. | |
| 2017/0196769 A1 | 7/2017 | Freeman et al. | |
| 2017/0197972 A1 | 7/2017 | Gosmini et al. | |
| 2017/0202510 A1 | 7/2017 | Freeman et al. | |
| 2017/0202733 A1 | 7/2017 | Freeman | |
| 2017/0225002 A1 | 8/2017 | Freeman | |
| 2017/0303796 A1* | 10/2017 | Tanabe | A61B 5/02416 |
| 2019/0254594 A1 | 8/2019 | Freeman et al. | |

FOREIGN PATENT DOCUMENTS

| | | |
|---|---|---|
| JP | 2003-521355 A | 7/2003 |
| JP | 2005-278758 A | 10/2005 |
| JP | 2008-512167 A | 4/2008 |
| JP | 2008-514263 A | 5/2008 |
| JP | 2012-61361 A | 3/2012 |
| JP | 2013-510123 A | 3/2013 |
| JP | 2014-168579 A | 9/2014 |
| WO | 2014202829 A1 | 12/2014 |

OTHER PUBLICATIONS

International Search Report, issued by International Searching Authority in corresponding International Application No. PCT/JP2016/003318, dated Nov. 18, 2016, (PCT/ISA/210).
Written Opinion, issued by International Searching Authority in corresponding International Application No. PCT/JP2016/003318, dated Nov. 18, 2016, (PCT/ISA/237).
Communication dated Mar. 27, 2020 from the State Intellectual Property Office of the P.R.C. in application No. 201680042202.X.
Communication dated Dec. 2, 2020, from the State Intellectual Property Office of People's Republic of China in counterpart Application No. 201680042202.X.

* cited by examiner

LIFESAVING ASSISTING APPARATUS

TECHNICAL FIELD

The present disclosure relates to a lifesaving assisting apparatus for determining whether to perform an act of lifesaving.

Use of an AED (Automatic External Defibrillator) can be exemplified as an act of lifesaving. The AED is an apparatus which delivers an electric shock to a patient in which fatal arrhythmia such as ventricular fibrillation or pulseless ventricular tachycardia has been detected, in order to revive the patient. Specifically, when the patient has no consciousness and respiration, electrode pads of the AED are pasted on the naked chest of the patient. The AED analyzes an electrocardiogram acquired through the electrode pads to detect the fatal arrhythmia (for example, see Patent Literature 1).

CITATION LIST

Patent Literature

[PTL 1] Japanese Patent Publication No. 2012-061361A

SUMMARY OF INVENTION

Technical Problem

In a case where a general citizen who is not a health care provider encounters a patient falling down in front of the citizen, even if the citizen can bring the AED to the patient, the citizen tends to hesitate about using the AED. Particularly, a patient who is in an agonal stage has unique respiration called gasping respiration though the patient is in a cardiopulmonary arrest state. Therefore, it is difficult for the citizen to accurately judge an unconscious and breathless state. As a result, the citizen may delay applying an electric shock to the patient. This contributes to the lowering of a lifesaving rate.

In addition, unconscious patients include patients caused by encephalophy, low blood sugar, hemorrhagic shock, drowning, carbon monoxide poisoning, etc. Although it is unnecessary to use the AED on such a patient, it is difficult for a general citizen to make an accurate judgment on this. Accordingly, in some cases, privacy of the patient may be unable to be sufficiently protected because the chest of the patient is made naked unnecessarily in front of the general public. In addition, the necessity of a measure to make the chest naked also contributes to the hesitation of a lifesaver in using the AED.

Accordingly, there is an object to provide a lifesaver with proper information about whether to perform an act of lifesaving in order to assist the lifesaver while taking privacy of a patient into consideration.

Solution to Problem

In order to achieve the object, there is provided a lifesaving assisting apparatus comprising:

a light-emitting section configured to emit light to be irradiated on a body of a patient;

a light-receiving section configured to output a signal corresponding to an intensity of light which has been transmitted through or reflected from the body of the patient;

a pulse-amplitude Index acquiring section configured to analyze amplitude of the signal to acquire a pulse-amplitude Index of the patient;

a pulse determining section configured to determine presence or absence of a pulse of the patient in accordance with the pulse-amplitude Index; and a notifying section configured to notify a result of determination made by the pulse determining section.

It is difficult even for an expert to judge presence or absence of the pulse accurately and rapidly. Particularly, a patient who is in an agonal stage has unique respiration called gasping respiration though the patient is in a cardiopulmonary arrest state. Therefore, there may be a case where presence of the pulse may be judged based on the fact of breathing. According to the above configuration, an objective parameter which is the pulse-amplitude Index of the patient is used. Accordingly, presence or absence of the pulse of the patient can be determined accurately no matter who handles the lifesaving assisting apparatus. In addition, presence or absence of the pulse can be determined by the pulse determining section as long as a pulse wave signal corresponding to several cycles to about ten cycles can be acquired. Accordingly, presence or absence of the pulse of the patient can be determined rapidly no matter who handles the lifesaving assisting apparatus.

A lifesaver can be notified of an accurate determination result about presence or absence of the pulse of the patient. Accordingly, for example, the lifesaver can avoid unnecessarily undressing the patient when it is not necessary to use the AED. In this manner, it is possible to protect privacy of the patient. Thus, it is possible to provide the lifesaver with proper information about whether to perform an act of lifesaving in order to assist the lifesaver while taking the privacy of the patient into consideration.

DESCRIPTION OF EMBODIMENT

Exemplary embodiments will be described below in detail with reference to the accompanying drawings. The respective drawings which will be used in the following description are changed in scale suitably to make the sizes of respective members recognizable.

Figure 1:
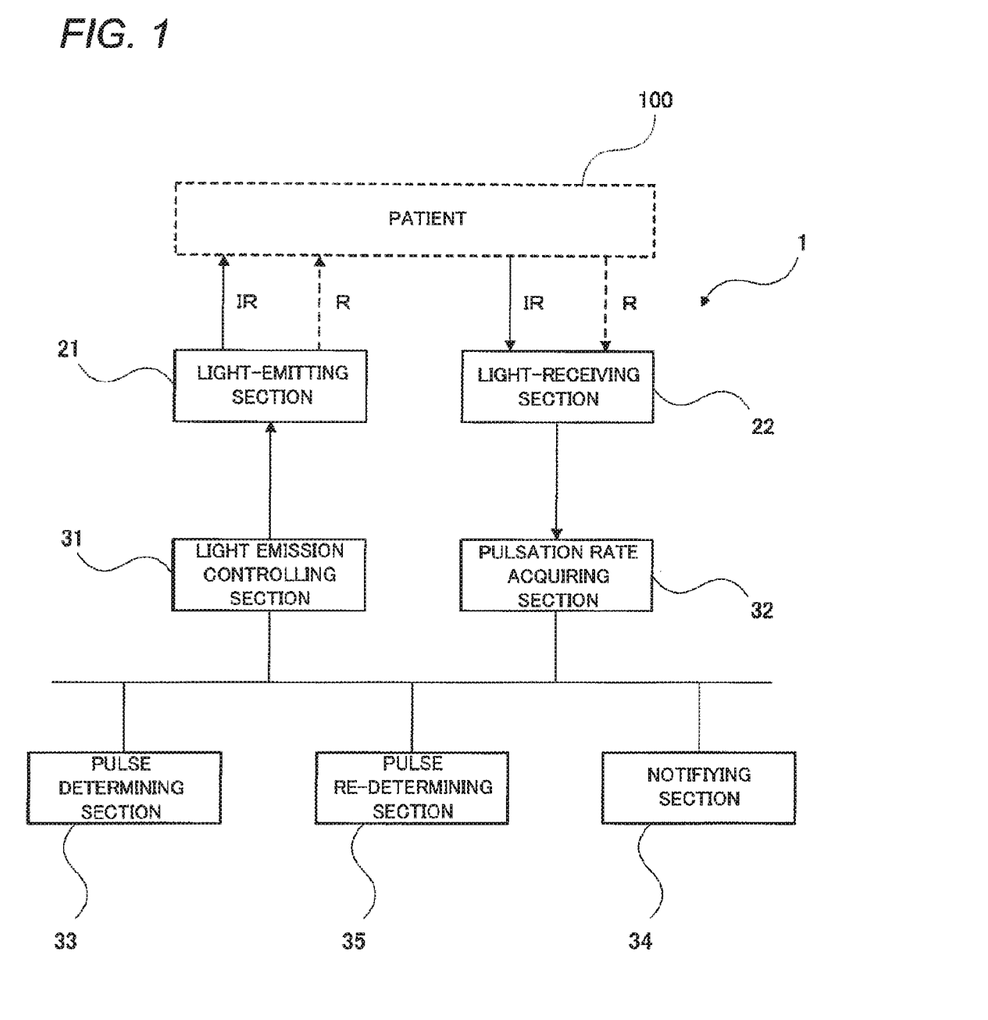
FIG. 1 is a diagram showing the functional configuration of a lifesaving assisting apparatus according to one embodiment.

FIG. 1 shows the functional configuration of a lifesaving assisting apparatus 1 according to one embodiment. The lifesaving assisting apparatus 1 is an apparatus which detects presence or absence of a pulse of a patient 100 to thereby determine whether to perform an act of lifesaving.

The lifesaving assisting apparatus 1 is provided with a light-emitting section 21. The light-emitting section 21 is configured to emit light to be irradiated on the body of the patient 100. The body of the patient 100 means tissues where a blood flow exists. For example, a semiconductor light-emitting element which can emit light having a predetermined wavelength may be used as the light-emitting section 21. Examples of the semiconductor light-emitting element include a light-emitting diode (LED), a laser diode, an organic EL element, etc. Infrared light IR and red light R may be used as examples of the light having the predetermined wavelength.

The lifesaving assisting apparatus 1 is provided with a light emission controlling section 31. The light emission controlling section 31 is configured to control switching on/off of a light source in the light-emitting section 21.

The lifesaving assisting apparatus 1 is provided with a light-receiving section 22. The light-receiving section 22 is configured to output a signal corresponding to intensity of the light transmitted through or reflected from the body of the patient 100. For example, an optical sensor having sensitivity to the wavelength of the light emitted from the light-emitting section 21 may be used as the light-receiving section 22. Examples of the optical sensor include a photodiode, a phototransistor and a photoresistor.

The lifesaving assisting apparatus 1 is provided with a pulse-amplitude Index acquiring section 32. The pulse-amplitude Index acquiring section 32 is configured to analyze amplitude of a signal outputted from the light-receiving section 22 to acquire a pulse-amplitude Index of the patient 100. The pulse-amplitude Index will be described with reference to FIG. 2A.

Figure 2A:
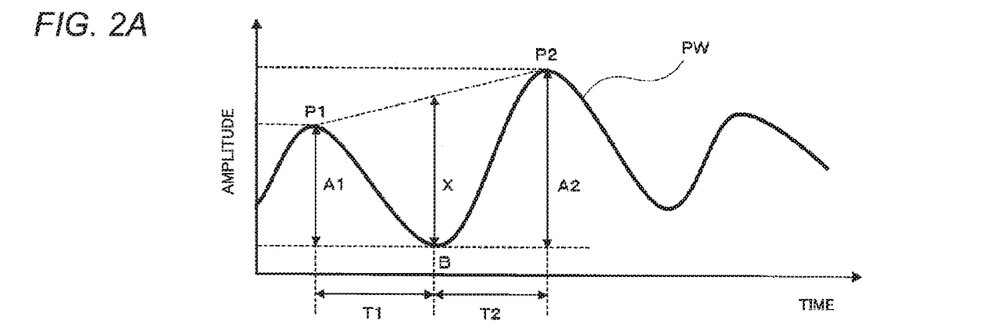
FIG. 2A is a diagram for explaining a definition of a pulse rate.

When the patient 100 has a pulse, a blood amount in the tissues on which the light is irradiated by the light-emitting section 21 changes. Accordingly, the intensity of the light detected by the light-receiving section 22 changes, and the amplitude of the signal outputted from the light-receiving section 22 changes. That is, the signal outputted from the light-receiving section 22 is a pulse wave.

The pulse-amplitude Index acquiring section 32 is provided with a filter which extracts a DC component from the pulse wave. That is, the pulse-amplitude Index acquiring section 32 is configured to obtain a pulsating component and a non-pulsating component from the pulse wave signal outputted from the light-receiving section 22. When the light emitted from the light-emitting section 21 is infrared light IR or red light R, the pulsating component during the change of the intensity of the light detected by the light-receiving section 22 is mainly an amount of contribution from arterial blood, and the non-pulsating component is mainly an amount of contribution from the tissues or venous blood. The pulse-amplitude Index acquiring section 32 is configured to acquire a normalized pulse wave PW in order to eliminate a component depending on the patent 100 personally. The normalized pulse wave PW is obtained by dividing the pulsating component by the non-pulsating component.

Amplitude of the normalized pulse wave PW is defined as pulse-amplitude Index X. There is however a case where the amplitude may change between a maximum value P1 and a next maximum value P2 which exist before and behind a minimum value B of a certain specific wave because the normalized pulse wave PW drifts. On this occasion, the amplitude in the minimum value B takes a value between (P1-B) and (P2-B). Accordingly, the pulse-amplitude Index X can be expressed by the following expression by way of example.

$$X=(A1+A2)/2$$

Here, A1 designates a difference in amplitude (absolute value) between the maximum value P1 at a time point at which the amplitude of the normalized pulse wave PW takes the maximum value P1 and the minimum value B. A2 designates a difference in amplitude (absolute value) between the maximum value P2 at a time point at which the amplitude of the normalized pulse wave PW takes the maximum value P2 and the minimum value B. That is, the pulse-amplitude Index X in the example is given as an average value of A1 and A2. However, the pulse-amplitude Index X may be set at any value between A1 and A2.

Similarly, the pulse-amplitude Index acquiring section 32 acquires a pulse-amplitude Index X as to a next signal cycle defined by the maximum value P2 and a maximum value P3. The pulse-amplitude Index acquiring section 32 is configured to acquire a representative pulse-amplitude Index based on a plurality of pulse-amplitude Indices X acquired thus within a predetermined period. The representative pulse-amplitude Index is defined as an average value of the plurality of pulse-amplitude Indices X.

Incidentally, in order to acquire the representative pulse-amplitude Index, it is preferable that samples accounting for a predetermined percentage are removed from the plurality of pulse-amplitude Indices X acquired within the predetermined period and an average value of the remaining samples is obtained. For example, top 25% may be used as the predetermined percentage. For example, in a case where eight samples have been acquired, two samples are removed in descending order in the value of the pulse-amplitude Index X from the eight samples and a representative pulse-amplitude Index is obtained as an average value of the remaining six samples.

The lifesaving assisting apparatus 1 is provided with a pulse determining section 33. The pulse determining section 33 is configured to determine presence or absence of the pulse of the patient 100 based on the pulse-amplitude Indices X acquired by the pulse-amplitude Index acquiring section 32. Specifically, the pulse determining section 33 is configured to determine presence or absence of the pulse of the patient 100 based on whether the representative pulse-amplitude Index acquired by the pulse-amplitude Index acquiring section 32 is lower than a predetermined threshold. For example, 1% may be used as the threshold. The pulse determining section 33 is configured as follows. That is, in a case where the representative pulse-amplitude Index is lower than the threshold, the pulse determining section 33 determines that the patient 100 has no pulse. When the representative pulse-amplitude Index is no lower than the threshold, the pulse determining section 33 determines that the patient 100 has a pulse.

The lifesaving assisting apparatus 1 is provided with a notifying section 34. The notifying section 34 is configured to notify a result of the determination made by the pulse determining section 33. The notification is performed by at least one of optical notification (light emission of an LED, display of a message on a display device, etc.), acoustic notification (a guidance message, a melody, a beep, etc.), and vibratory notification.

As described above, there are various reasons causing the patient's syncope. In some cases, it is not necessary to use the AED to deliver an electric shock. Cardiogenic syncope belongs to a case in which an electric shock does not have to be delivered. The cardiogenic syncope can be judged based on the fact that there is no pulse. Syncope caused by encephalopathy, massive bleeding, low blood sugar, anemia, hypocapnia, etc. belongs to a case in which an electric shock does not have to (or must not) be delivered. Such cardiogenic syncope can be judged based on the fact that there is a pulse.

However, it is difficult even for an expert to judge presence or absence of the pulse accurately and rapidly. Particularly, a patient who is in an agonal stage has unique respiration called gasping respiration though the patient is in a cardiopulmonary arrest state. Therefore, there may be a case where presence of the pulse may be judged based on the fact of breathing. According to the configuration of the lifesaving assisting apparatus 1 according to the embodiment, an objective parameter which is the pulse-amplitude Index X of the patient 100 is used. Accordingly, presence or absence of the pulse of the patient 100 can be determined accurately no matter who handles the lifesaving assisting apparatus 1. In addition, presence or absence of the pulse can be determined by the pulse determining section 33 as long as a pulse wave signal corresponding to several cycles to about ten cycles can be acquired. Accordingly, presence or absence of the pulse of the patient 100 can be determined rapidly no matter who handles the lifesaving assisting apparatus 1.

The lifesaver can be notified of an accurate determination result about presence or absence of the pulse of the patient 100. Accordingly, for example, the lifesaver can avoid unnecessarily undressing the patient 100 when it is not necessary to use the AED. In this manner, it is possible to protect privacy of the patient 100. Thus, it is possible to provide the lifesaver with proper information about whether to perform an act of lifesaving in order to assist the lifesaver while taking the privacy of the patient into consideration.

The pulse-amplitude Index acquiring section 32 is configured to acquire the pulse-amplitude Index X based on the infrared light IR emitted from the light-emitting section 21.

According to such a configuration, a light source used in a probe of a pulse oximeter generally used in critical care can be used. It is unnecessary to prepare a separate light source. Therefore, it is possible to suppress the total cost for providing the lifesaving assisting apparatus 1. In addition, the infrared light is hardly affected by the color of skin when it is transmitted through or reflected from the body of the patient 100. In this manner, accuracy of the acquired pulse-amplitude Index X is improved, and accuracy of determination of presence or absence of the pulse made by the pulse determining section 33 in the subsequent stage is also improved. Accordingly, it is possible to provide the lifesaver with more proper information about whether to perform an act of lifesaving in order to assist the lifesaver while taking the privacy of the patient into consideration.

The pulse determining section 33 may be configured to determine presence or absence of the pulse of the patient 100 based on not only the aforementioned pulse-amplitude Index X but also an inflection point number N within a predetermined time duration in the signal outputted from the light-receiving section 22. For example, one second may be used as the predetermined time duration.

Figure 2B:
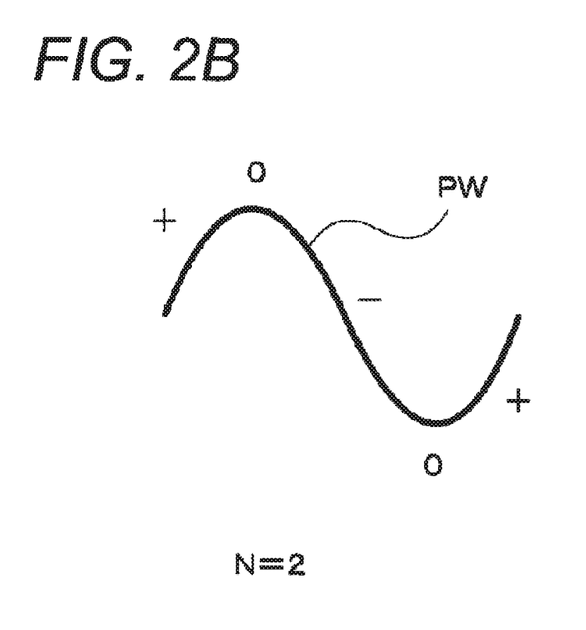
FIG. 2B is a diagram for explaining a definition of an inflection point number.
Figure 2C:
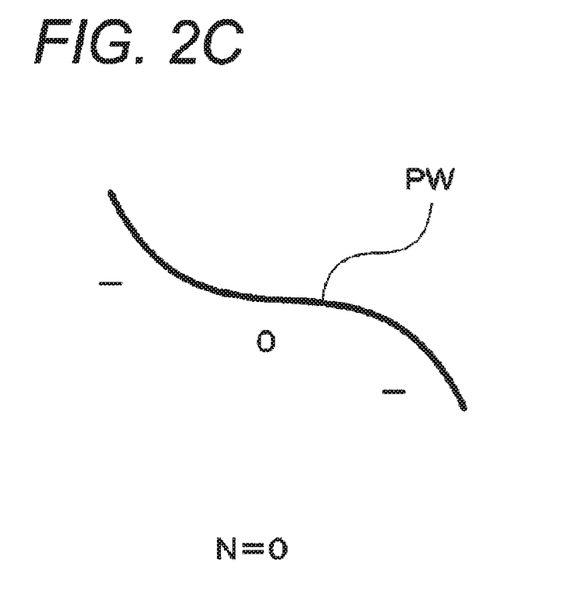
FIG. 2C is a diagram for explaining the definition of the inflection point number.
Figure 2D:
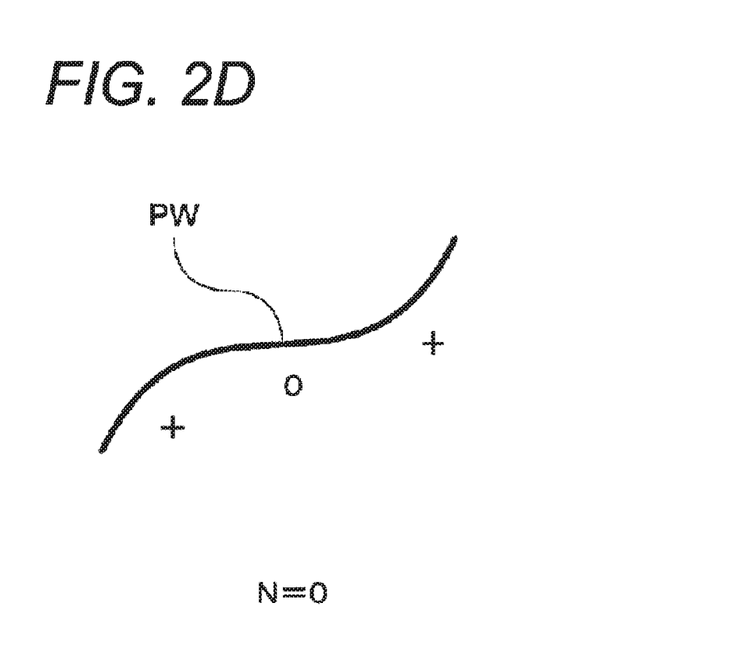
FIG. 2D is a diagram for explaining the definition of the inflection point number.

As shown in FIGS. 2B, 2C and 2D, the "inflection point number" herein is defined as the number of times in which a differential value of a normalized pulse wave PW alternates between positive and negative. In the example shown in FIG. 2B, the differential value of the normalized pulse wave PW changes from positive to negative and changes to positive again. Accordingly, the inflection point number N is 2. On the other hand, in the examples shown in FIGS. 2C and 2D, the differential value of the normalized pulse wave PW reaches zero in the middle but does not alternate between positive and negative before and behind the zero. Accordingly, the inflection point number N is 0.

Figure 3A:
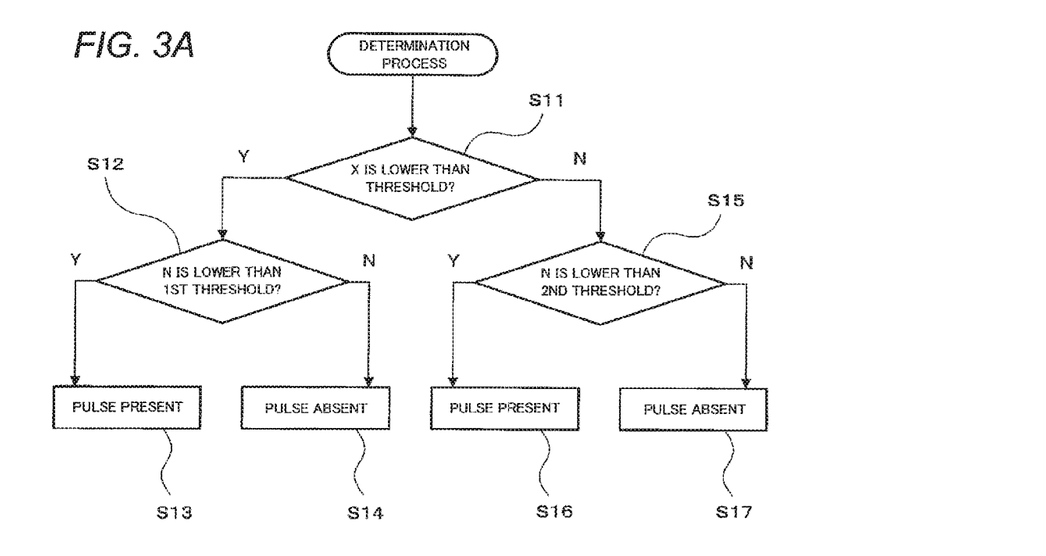
FIG. 3A is a flowchart showing process performed by the lifesaving assisting apparatus of FIG. 1.

FIG. 3A is a flowchart showing a determination process performed by the pulse determining section 33 in this embodiment. First, the pulse determining section 33 determines whether the pulse-amplitude Index X (representative pulse-amplitude Index) of the patient 100 acquired by the pulse-amplitude Index acquiring section 32 is lower than a predetermined threshold (step S11).

When it is determined that the pulse-amplitude Index X is lower than the predetermined threshold (Y in the step S11), the pulse determining section 33 counts the inflection point number N of the normalized pulse wave PW in a predetermined period, and determines whether the inflection point number N is lower than a first threshold (step S12). For example, 10 may be used as the first threshold.

When it is determined that the inflection point number N is lower than the first threshold (Y in the step S12), the pulse determining section 33 determines that the patient 100 has a pulse (step S13). This situation means that the result determined as absence of the pulse based on the pulse-amplitude Index X is reversed by the determination based on the inflection point number N.

When it is determined that the inflection point number N is no lower than the first threshold (N in the step S12), the pulse determining section 33 determines that the patient 100 has no pulse (step S14). This situation means that the result determined as absence of the pulse based on the pulse-amplitude Index X is confirmed by the determination based on the inflection point number N.

When it is determined that the pulse-amplitude Index X is no lower than the predetermined threshold (N in the step S11), the pulse determining section 33 counts the inflection point number N of the normalized pulse wave PW within the predetermined period and determines whether the inflection point number N is lower than a second threshold (step S15). For example, 15 may be used as the second threshold.

When it is determined that the inflection point number N is lower than the second threshold (Y in the step S15), the pulse determining section 33 determines that the patient 100 has a pulse (step S16). This situation means that the result determined as presence of the pulse based on the pulse-amplitude Index X is confirmed by the determination based on the inflection point number N.

When it is determined that the inflection point number N is no lower than the second threshold (N in the step S15), the pulse determining section 33 determines that the patient 100 has no pulse (step S17). This situation means that the result determined as presence of the pulse based on the pulse-amplitude Index X is reversed by the determination based on the inflection point number N.

Figure 3B:
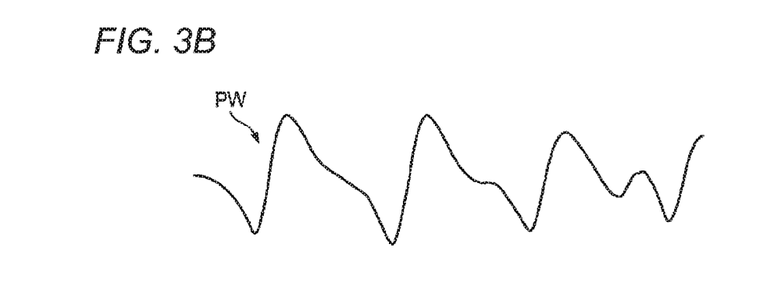
FIG. 3B is a diagram showing a typical normalized pulse wave determined as presence of the pulse.
Figure 3C:
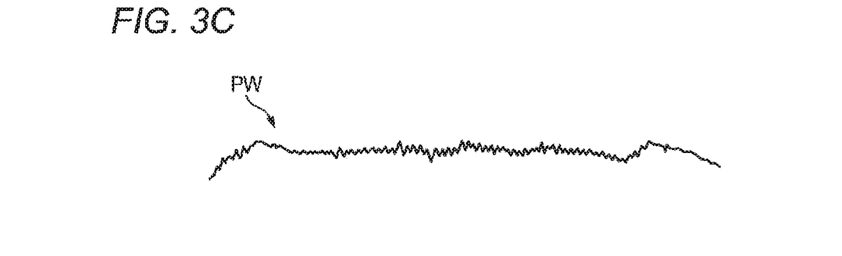
FIG. 3C is a diagram showing a typical normalized pulse wave determined as absence of the pulse.

FIG. 3B shows a typical normalized pulse wave PW determined as presence of the pulse. The inflection point number N in an illustrated period is lower than 10. FIG. 3C shows a typical normalized pulse wave PW determined as absence of the pulse. The inflection point number N in the illustrated period is higher than 100.

As shown in the situation of the step S13 or S17, the inflection point number N is added to determination criteria. In this manner, accuracy of determination of presence or absence of the pulse is improved. Accordingly, it is possible to provide the lifesaver with more proper information about whether to perform an act of lifesaving in order to assist the lifesaver while taking the privacy of the patient into consideration.

The pulse determining section 33 is configured to acquire the inflection point number N based on the infrared light IR emitted from the light-emitting section 21.

According to such a configuration, it is possible to use a light source used in a probe of a pulse oximeter generally used in critical care. It is therefore unnecessary to prepare a separate light source. Accordingly, it is possible to suppress the total cost for providing the lifesaving assisting apparatus 1. In addition, the infrared light is hardly affected by the color of skin when it is transmitted through or reflected from the body of the patient 100. In this manner, accuracy of the acquired inflection point number N is improved, and accuracy of determination of presence or absence of the pulse made by the pulse determining section 33 in the subsequent stage is also improved. Accordingly, it is possible to provide the lifesaver with more proper information about whether to perform an act of lifesaving in order to assist the lifesaver while taking the privacy of the patient into consideration.

As shown in FIG. 1, the lifesaving assisting apparatus 1 may be provided with a pulse re-determining section 35. In this case, the light-emitting section 21 is configured to emit infrared light IR and red light R. In addition, the light-receiving section 22 is configured to output signals respectively corresponding to intensities of the infrared light IR and the red light R transmitted through or reflected from the body of the patient 100. The pulse re-determining section 35 is configured as follows. That is, in a case where it is determined by the pulse determining section 33 that the patient 100 has a pulse, the pulse re-determining section 35 acquires arterial oxygen saturation (SpO2) and a heart rate of the patient 100 based on the signals outputted from the light-receiving section 22 and re-determines presence or absence of the pulse of the patient 100 based on these biological parameters.

A process for acquiring the arterial oxygen saturation and the heart rate from the intensities of the infrared light and the red light transmitted through or reflected from biological tissues is based on the principles of the pulse oximeter. Since the process per se is widely known, detailed description thereof will be omitted.

Figure 4A:
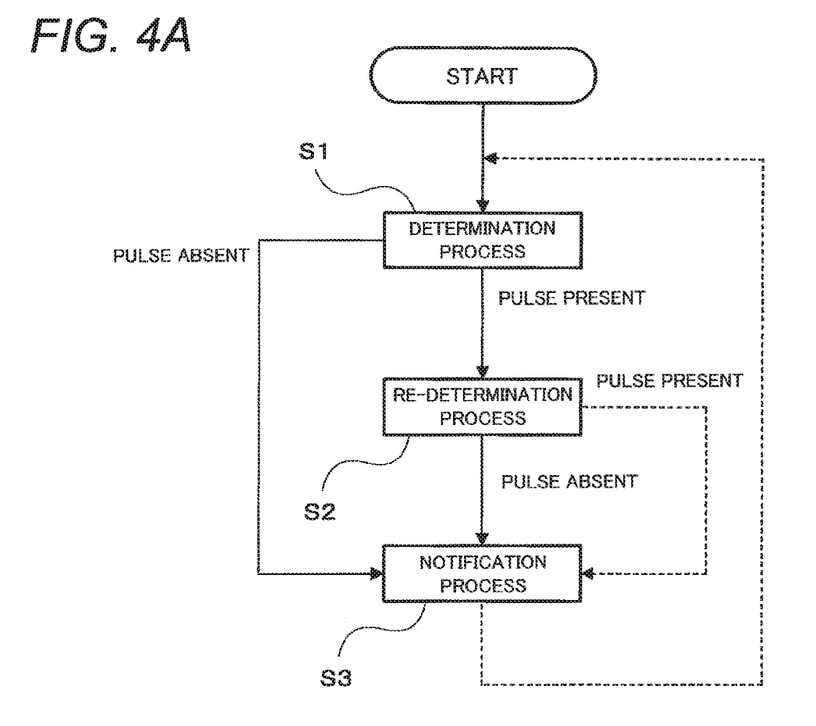
FIG. 4A is a flowchart showing process performed by the lifesaving assisting apparatus of FIG. 1.

FIG. 4A is a flowchart illustrating operation of the pulse re-determining section 35 in the example. As described previously, a determination process is performed by the pulse determining section 33 (step S1). When the determination process results in a conclusion that the patient 100 has a pulse, a re-determination process is executed by the pulse re-determining section 35 (step S2).

Figure 4B:
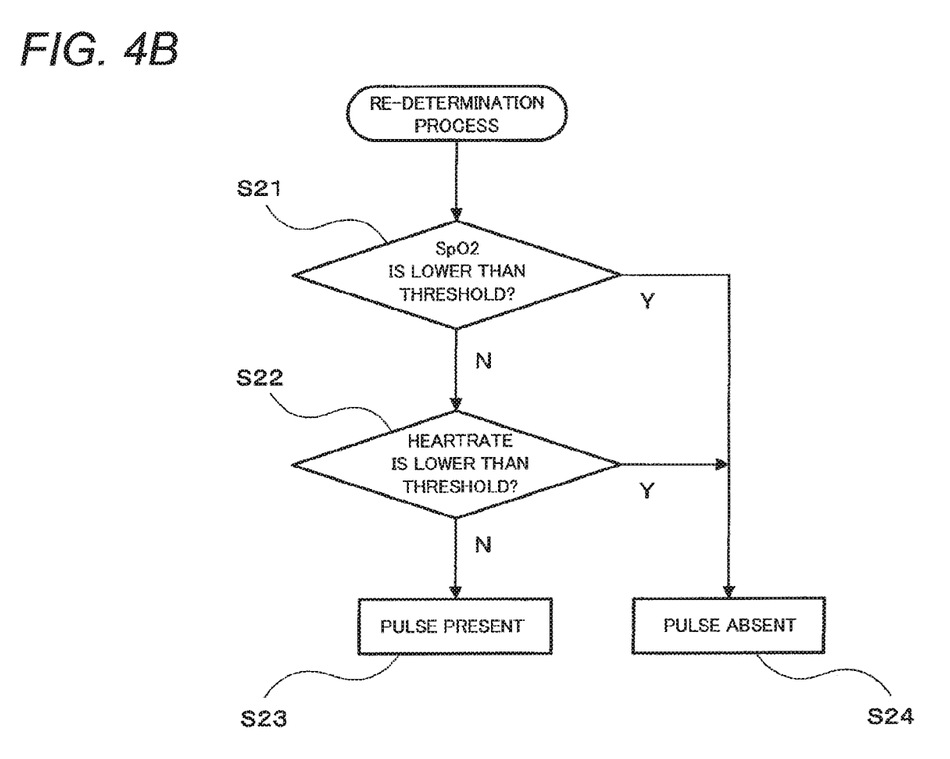
FIG. 4B is a flowchart showing process performed by the lifesaving assisting apparatus of FIG. 1.

FIG. 4B is a flowchart showing a specific flow of the re-determination process. First, the pulse re-determining section 35 determines whether the acquired arterial oxygen saturation of the patient 100 is lower than a predetermined threshold (step S21). For example, 85% may be used as the threshold.

When it is determined that the arterial oxygen saturation of the patient 100 is no lower than the threshold (N in the step S21), the pulse re-determining section 35 determines whether the acquired heart rate of the patient 100 is lower than a predetermined threshold (step S22). For example, 40 times per minute may be used as the threshold.

When it is determined that the heart rate of the patient 100 is no lower than the threshold (N in the step S22), the pulse re-determining section 35 determines that the patient 100 has a pulse (step S23). This situation means that the result determined as presence of the pulse by the pulse determining section 33 is confirmed by the re-determination made by the pulse re-determining section 35.

When it is determined that the arterial oxygen saturation of the patient 100 is lower than the predetermined threshold (Y in the step S21) or in a case where it is determined that the heart rate of the patient 100 is lower than the predetermined value (Y in the step S22), the pulse re-determining section 35 determines that the patient 100 has no pulse (step S24). This situation means that the result determined as presence of the pulse by the pulse determining section 33 is reversed by the re-determination made by the pulse re-determining section 35.

That is, the pulse re-determining section 35 provides a fail-safe function in the lifesaving assisting apparatus 1. In this manner, even when the patient 100 who should be essentially determined as having no pulse has been determined as having a pulse by the pulse determining section 33 for some reason, the patient 100 can be determined as having no pulse by the pulse re-determining section 35. Accordingly, it is possible to provide the lifesaver with more proper information about whether to perform an act of lifesaving in order to assist the lifesaver while taking the privacy of the patient into consideration.

In the re-determination process shown in FIG. 4B, the sequence of the determination about the arterial oxygen saturation (step S21) and the determination about the heart rate (step S22) may be reverse to each other. In addition, configuration may be made so that only one of the determination about the arterial oxygen saturation (step S21) and the determination about the heart rate (step S22) is performed.

Figure 5:
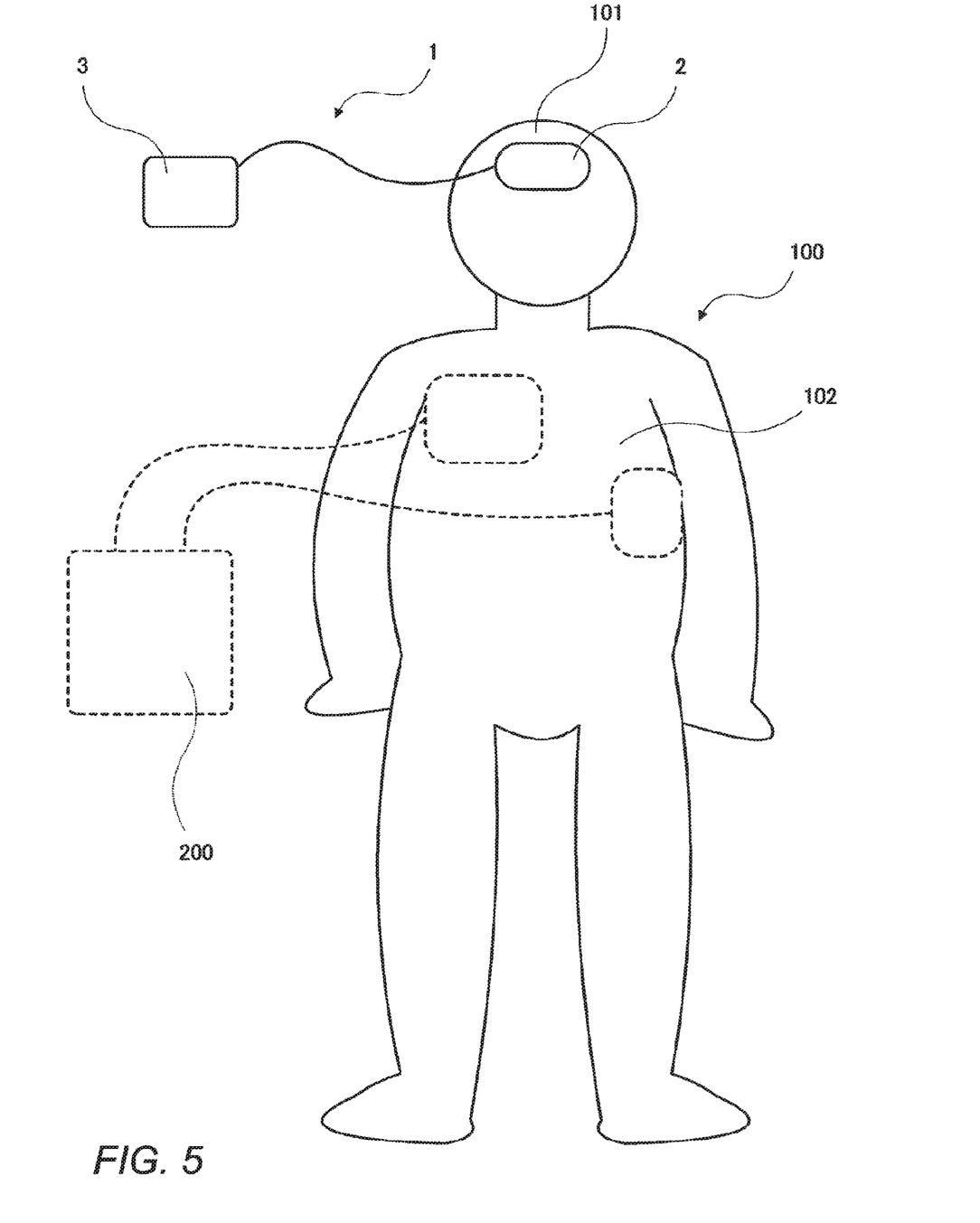
FIG. 5 is a diagram showing one example of how to use the lifesaving assisting apparatus of FIG. 1.

FIG. 5 schematically shows one example of how to use the lifesaving assisting apparatus 1. The lifesaving assisting apparatus 1 is provided with a probe 2 and a casing 3. The probe 2 includes the light-emitting section 21 and the light-receiving section 22. The light emission controlling section 31, the pulse-amplitude Index acquiring section 32, the pulse determining section 33, the notifying section 34 and the pulse re-determining section 35 are received in the casing 3.

The probe 2 including the light-emitting section 21 and the light-receiving section 22 is configured to be able to be mounted on a forehead 101 of the patient 100.

According to such a configuration, it is not necessary to undress the patient 100 when it is first determined whether the patient 100 has a pulse. In addition, the forehead 101 is a region which is hardly affected by body motion. It is therefore possible to improve accuracy of determination of presence or absence of the pulse. Accordingly, it is possible to provide the lifesaver with more proper information about whether to perform an act of lifesaving in order to assist the lifesaver while taking the privacy of the patient into consideration.

When the light-emitting section 21 is configured to emit infrared light or red light, a probe of a pulse oximeter can be used. Since a separate probe does not have to be prepared, it is possible to suppress the total cost for providing the lifesaving assisting apparatus 1.

As shown in FIG. 4A, the lifesaving assisting apparatus 1 executes a notification process (step S3) when the determination process (step S1) results in a conclusion that the patient 100 has no pulse or when the re-determination process (step S2) results in a conclusion that the patient 100 has no pulse. Specifically, the notifying section 34 provides information for promoting the lifesaver to use the AED. For example, voice guidance "No pulse can be detected. Please use AED." can be outputted. As shown in FIG. 5, the lifesaver mounts electrodes 201 of an AED 200 on a chest 102 of the patient 100 and executes a lifesaving measure in accordance with the voice guidance of the AED 200.

According to such a configuration, it is possible to expect an effect to strongly promote the hesitating lifesaver to use the AED 200. In addition, for example, the lifesaver may be replaced by another lifesaver who can use the AED 200. Thus, certainty of leading to use of the AED 200 can be improved.

In addition to or in place of this, the notifying section 34 provides information for promoting the lifesaver to perform sternum compressions. For example, voice guidance "No pulse can be detected. Please perform sternum compressions." can be outputted. The lifesaver performs sternum compressions on the chest 102 of the patient 100.

According to such a configuration, it is possible to expect an effect to strongly promote the hesitating lifesaver to perform a specific action. In addition, for example, the lifesaver may be replaced by another lifesaver who can perform a measure. Thus, certainty of leading to lifesaving can be improved.

Even after determining that the patient 100 has no pulse, the pulse determining section 33 can continuously perform the determination process for determining presence or absence of the pulse. In this case, the notifying section 34 may be configured to provide information for promoting the lifesaver to suspend performance of sternum compressions in a case where it is determined that the patient 100 has a pulse although it has been once determined as having no pulse. For example, voice guidance "Pulse has been restarted. Please do not perform sternum compressions." can be outputted.

According to such a configuration, it is possible to properly deal with the case where the condition of the patient 100 determined once as having no pulse has been improved. That is, it is possible to avoid performing unnecessary chest compressions on the patient 100 whose heart has restarted beating. Accordingly, it is possible to prevent an unnecessary load from being imposed on the sternum of the patient 100.

When the re-determination process (step S2) made by the pulse re-determining section 35 results in a conclusion that the patient 100 has a pulse as designated by a dashed line in FIG. 4A, the lifesaving assisting apparatus 1 may perform the notification process (step S3) for sending notification of the fact that the patient 100 has a pulse. Then, the lifesaving assisting apparatus 1 re-execute the determination process (step S1) with the pulse determining section 33. In other words, the pulse determining section 33 continuously performs the determination process for determining presence or absence of the pulse even after determining that the patient 100 has a pulse.

According to such a configuration, it is possible to properly deal with the case where the condition of the patient 100 who was determined once as having a pulse has changed suddenly. That is, the aforementioned notification process is performed in a case where the determination process performed continuously results in a conclusion that the patient 100 has fallen into a no-pulse condition.

In the embodiment, the functions of the light emission controlling section 31, the pulse-amplitude Index acquiring section 32, the pulse determining section 33, the notifying section 34 and the pulse re-determining section 35 are at least partially achieved by software executed by the cooperation of a processor and a memory which are connected to each other communicably. A CPU or an MPU may be used as the processor by way of example. An RAM or an ROM may be used as the memory by way of example. However, the functions of the light emission controlling section 31, the pulse-amplitude Index acquiring section 32, the pulse determining section 33, the notifying section 34 and the pulse re-determining section 35 may be at least partially achieved by hardware such as an ASIC and an FPGA, or by a combination of hardware and software.

The aforementioned embodiment is merely exemplified in order to make the disclosed concept easy to understand. The configuration according to the aforementioned embodiment can be changed or modified suitably without departing from the disclosed concept. In addition, it is obvious that equivalents are contained in the claimed scope.

Only the infrared light IR is used for acquiring the pulse-amplitude Index X and the inflection point number N in the aforementioned embodiment. However, both the infrared light IR and the red light R may be used for acquiring the pulse-amplitude Index X and the inflection point number N, or only the red light R may be used for acquiring the pulse-amplitude Index X and the inflection point number N. Switching on/off of light sources for emitting the respective lights may be controlled suitably by the light emission controlling section 31.

The region where the probe 2 is mounted does not have to be always the forehead 101 of the patient 100. A transmissive type pulse oximeter may be configured to be mounted on the tip of a finger, the tip of a toe, an ear, etc. Also in the case, it is possible to determine presence or absence of the pulse without undressing the patient 100.

The probe 2 does not have to be always a probe of a pulse oximeter. As long as information about the blood flow can be acquired, the probe 2 may be configured as at least a part of an instrument (an ultrasonic blood flowmeter, an electromagnetic blood flowmeter, a laser blood flowmeter, a Doppler blood flowmeter, etc.) using any of an ultrasonic wave, an electromagnetic wave and laser light. In this case, the probe 2 may be mounted on a neck portion, an arm portion or a leg portion of the patient 100. In any case, it is possible to determine presence or absence of the pulse while suppressing exposure of the skin of the patient 100 to the minimum.

The example in which the lifesaver is promoted to use the AED 200 by the notifying section 34 has been described in the aforementioned embodiment. The notifying section 34 may be configured to promote the lifesaver to use not just the AED 200 but any general defibrillator.

The present application is based on Japanese Patent Application No. 2015-143008 filed on Jul. 17, 2015 and Japanese Patent Application No. 2016-096356 filed on May 12, 2016, the contents of which are hereby incorporated by reference.

The invention claimed is:

1. A lifesaving assisting apparatus comprising:
an optical emitter configured to emit light to be irradiated on a body of a patient;
an optical receiver configured to output a signal corresponding to an intensity of light which has been transmitted through or reflected from the body of the patient; and
a processor configured to acquire a pulse-amplitude Index of the patient based on an amplitude of the signal, determine an inflection point number of the signal per unit time, wherein the inflection point number is a number of times in which a differential value of a normalized pulse wave of the signal alternates between positive and negative, and determine presence or absence of a pulse of the patient in accordance with the pulse-amplitude Index and the inflection point number, and control output of a result indicating the presence or the absence of the pulse of the patient.

2. The lifesaving assisting apparatus according to claim 1, wherein the processor is configured to determine the presence or the absence of the pulse of the patient based on whether the pulse-amplitude Index of the patient is greater than or less than a threshold, when the pulse-amplitude Index of the patient is greater than the threshold, the processor is further configured to determine whether the inflection point number of the signal is greater than or less than a first threshold, and when the pulse-amplitude Index of the patient is less than the threshold, the processor is further configured to determine whether the inflection point number of the signal is greater than or less than a second threshold.

3. The lifesaving assisting apparatus according to claim 2, wherein the optical emitter is configured to emit infrared light as the light, and
wherein the processor is configured to acquire the pulse-amplitude Index and the inflection point number in accordance with the infrared light.

4. The lifesaving assisting apparatus according to claim 1, wherein the optical emitter is configured to emit infrared light as the light, and
wherein the processor is configured to acquire the pulse-amplitude Index and the inflection point number in accordance with the infrared light.

5. The lifesaving assisting apparatus according to claim 1, wherein the optical emitter and the optical receiver are configured to be attached on a forehead of the patient.

6. The lifesaving assisting apparatus according to claim 1, wherein the processor is configured to provide information promoting usage of a defibrillator, in a case of the absence of the pulse of the patient.

7. The lifesaving assisting apparatus according to claim 1, wherein the processor is configured to provide information promoting to perform sternum compressions, in a case of the absence of the pulse of the patient.

8. The lifesaving assisting apparatus according to claim 1, wherein the processor is configured to continuously determine the presence or the absence of the pulse.

9. The lifesaving assisting apparatus according to claim 1, wherein the processor is configured to provide information promoting to suspend performance of sternum compressions, in a case of the presence of the pulse of the patient after a case of the absence of the pulse of the patient.

10. A lifesaving assisting apparatus comprising:
an optical emitter configured to emit light to be irradiated on a body of a patient, wherein the light comprises infrared light and red light;
an optical receiver configured to output a signal corresponding to an intensity of light which has been transmitted through or reflected from the body of the patient; and
a processor configured to acquire a pulse-amplitude Index of the patient based on an amplitude of the signal, determine an inflection point number of the signal per unit time, wherein the inflection point number is a number of times in which a differential value of a normalized pulse wave of the signal alternates between positive and negative, determine at least one of arterial oxygen saturation and a heart rate obtained from the signal, and determine presence or absence of a pulse of the patient in accordance with the pulse-amplitude Index, the inflection point number, and the at least one of the arterial oxygen saturation and the heart rate control output of a result indicating the presence or the absence of the pulse of the patient.

* * * * *